US00RE35633E

United States Patent [19]

Leyshon

[11] E Patent Number: Re. 35,633

[45] Reissued Date of Patent: Oct. 14, 1997

[54] METHANE CONVERSION PROCESS

[75] Inventor: David W. Leyshon, West Chester, Pa.

[73] Assignee: Atlantic Richfield Company, Los Angeles, Calif.

[21] Appl. No.: 375,342

[22] Filed: Jan. 19, 1995

Related U.S. Patent Documents

Reissue of:

[64] Patent No.: 4,801,762
Issued: Jan. 31, 1989
Appl. No.: 14,405
Filed: Feb. 13, 1987

U.S. Applications:

[62] Division of Ser. No. 6,421, Jan. 19, 1993.

[51] Int. Cl.[6] ..... C07C 2/00

[52] U.S. Cl. ..... 585/500; 585/415; 585/417; 585/418; 585/654; 585/656; 585/658; 585/661; 585/943; 585/833; 585/905

[58] Field of Search ..... 585/500, 654, 585/656, 661, 700, 943, 400, 415, 417, 418

[56] References Cited

U.S. PATENT DOCUMENTS

| | | | |
|---|---|---|---|
| 4,523,049 | 6/1985 | Jones et al. | 585/500 |
| 4,547,610 | 10/1985 | Sofranko | 585/656 X |
| 4,654,460 | 3/1987 | Kimble | 585/500 |
| 4,658,076 | 4/1987 | Kolts | 585/500 |
| 4,665,259 | 5/1987 | Brezdil | 585/500 |
| 4,670,619 | 6/1987 | Withers | 585/943 X |
| 4,678,862 | 7/1987 | Mazurek | 585/500 |
| 4,769,508 | 9/1988 | Gastinger et al. | 585/943 |
| 4,795,848 | 1/1989 | Toker | 585/500 |
| 5,087,787 | 2/1992 | Kimble et al. | 585/415 |

FOREIGN PATENT DOCUMENTS 0189079 7/1986 European Pat. Off. .

OTHER PUBLICATIONS

Otsuka, Chem. Soc. of Japan, Chemical Letters (1986) pp. 903–906 (1986).

Lin et al, "Oxidative Dimerization of Methane over Lanthanum Oxide", J. Phys. Chem., vol. 90, No. 4, Feb. 1986, pp. 534–537.

Ito et al, "Oxidative Dimerization of Methane over a Lithium Promoted Magnesium Oxide Catalyst", J. Am. Chem. Soc., vol. 107, 1985, pp. 5062–5068.

Kimble, James B. et al., "Oxidative Coupling of Methane to Higher Hydrocarbons," Amer. Inst. of Chem. Engrs. meeting in New Orleans, Apr. 6–10, 1986.

*Primary Examiner*—Asok Pal
*Attorney, Agent, or Firm*—William C. Long

[57] ABSTRACT

In an improved method for converting methane to at least one higher hydrocarbon product and coproduct water which comprises contacting a gas comprising methane and at least one added gaseous oxidant with nonacidic solid, the improvement comprising conducting at least a portion of said contacting in the presence of added water.

8 Claims, 2 Drawing Sheets

METHANE CONVERSION PROCESS

Matter enclosed in heavy brackets [ ] appears in the original patent but forms no part of this reissue specification; matter printed in italics indicates the additions made by reissue.

*CROSS REFERENCE TO RELATED APPLICATION*

*This is a divisional of Ser. No. 08/006,421 filed on Jan. 19, 1993 which is a Reissue application of U.S. Pat. No. 4,801,762.*

BACKGROUND OF THE INVENTION

This invention relates to the conversion of methane to higher hydrocarbons. A particular application of this invention is a method for converting natural gas to more readily transportable material.

Recently, it has been discovered that methane may be converted to higher hydrocarbons by a process which comprises contacting methane and an oxidative synthesizing agent at synthesizing conditions (e.g., at a temperature selected within the range from about 500° to about 1000° C.) Oxidative synthesizing agents are compositions having as a principal component at least one oxide of at least one metal which compositions product $C_{2+}$ hydrocarbon products, co-product water, and a composition comprising a reduced metal oxide when contacted with methane at synthesizing conditions. Reducible oxides of several metals have been identified which are capable of converting methane to higher hydrocarbons. In particular, oxides of manganese, tin, indium, germanium, lead, antimony, bismuth, praseodymium, terbium, cerium, iron and ruthenium are most useful. See commonly-assigned U.S. Pat. Nos. 4,443,649 (Mn); 4,444,984 (Sn); 4,445,648 (In); 4,443,645 (Ge); 4,443,674 (Pb); 4,443,646 (Bi); 4,499,323 (Pr); 4,499,324 (Ce); and 4,593,139 (Ru), the entire contents of which are incorporated herein by reference. See also commonly-assigned U.S. patent application Ser. No. 666,694 (Fe) the entire content of which is incorporated herein by reference.

Commonly-assigned U.S. Pat. No. 4,554,395 discloses and claims a process which comprises contacting methane with an oxidative synthesizing agent under elevated pressure (2–100 atmospheres) to produce greater amounts of $C_{3+}$ hydrocarbon products Commonly-assigned U.S. Pat. No. 4,560,821 discloses and claims a process for the conversion of methane to higher hydrocarbons which comprises contacting methane with particles comprising an oxidative synthesizing agent which particles recirculate between two physically separate zones—a methane contact zone and an oxygen contact zone.

U.S. Pat. No. 4,499,322 discloses and claims a process for the conversion of methane to higher hydrocarbon and comprises contacting methane with an oxidative synthesizing agent containing a promoting amount of alkali metal and/or compounds thereof.

U.S. Pat. No. 4,495,374 discloses and claims a process for the conversion of methane to higher hydrocarbons which comprises contacting methane with an oxidative synthesizing agent containing a promoting amount of alkaline earth metal and/or compounds thereof.

Hinsen and Baerns report studies of a continuous mode for the oxidative coupling of methane wherein regeneration air is cofed with methane feed. Hinsen, W. and Baerns, M., "Oxidative Koppling von Methan zu $C_{2-}$ Kohlenwassertoffen in Gegenwart unterschiedlicher Katalsatoren", Chemiker-Zeitung, Vol. 107, No. 718, pp. 223–226 (1983). Using a catalyst based on lead oxide and gamma-alumina in a fixed bed reactor operated at 1 atmosphere total pressure and 600–750 degrees C., they report results of approximately 53% selectivity to ethane and ethylene at 8% methane conversion for a feed consisting of about 50% methane, 25% air and 25% nitrogen. Other metal oxides studies by Hinsen and Baerns included oxides of Bi, Sb, Sn and Mn.

U.S. Pat. No 4,523,049, discloses and claims a process for converting methane to higher hydrocarbons which comprises contacting methane and an oxygen-containing gas with a solid comprising a reducible metal oxide and an alkali/alkaline earth metal promoter.

U.S. Pat. No. 4,523,050 discloses and claims a process for converting methane to higher hydrocarbons which comprises contacting methane and an oxygen-containing gas with a manganese silicate.

Commonly-assigned U.S. patent application Ser. No. 738,110, filed May 24, 1985, discloses and claims a method for converting methane to higher hydrocarbons wherein methane and a gaseous oxidant are contacted with a nonacidic solid. In a preferred embodiment, the solid comprises an alkali metal component associated with a support material. The application also teaches conducting the contacting in the presence of halogen promoters when employing alkali-promoted solids.

Commonly-assigned U.S. patent application Ser. No. 738,114, filed May 24, 1985, discloses and claims a process wherein methane and a gaseous oxidant are contacted with a nonacidic solid in the presence of halogen promoter but in the absence of an alkali metal promoter.

Concurrently-filed, commonly-assigned U.S. patent application Ser. No. 07/014,406 filed 2-13-87 discloses and claims a method for converting methane to higher hydrocarbons wherein methane and added water are contacted in the substantial absence of added gaseous oxidant with a solid comprising at least one reducible metal oxide.

The reaction product of the foregoing processes are hydrocarbons, carbon oxides, coke and water. It would be beneficial in these processes to reduce selectivities to carbon oxides and coke and to increase methane conversions to the desired hydrocarbon products. Accordingly, an object of this invention is to provide an improved process for converting methane to higher hydrocarbons. More particular aspects, objects and the several advantages of this invention will become apparent to those skilled in the art upon reading this disclosure and the appended claims.

SUMMARY OF THE INVENTION

It has been found that processes for producing higher hydrocarbons wherein methane and a gaseous oxidant are contacted with a nonacidic solid are improved when the contacting is conducted in the presence of added water. This added water is separate and apart from the coproduct water produced from methane conversion during the contacting. However, such coproduct water (or a portion thereof) may be separated from the other products and introduced into the contacting zone as the added water.

In processes conducted according to this invention, methane is converted to higher hydrocarbons with improved efficiency, e.g., increased selectivity to higher hydrocarbon products.

DETAILED DESCRIPTION OF THE INVENTION

Figure 1:
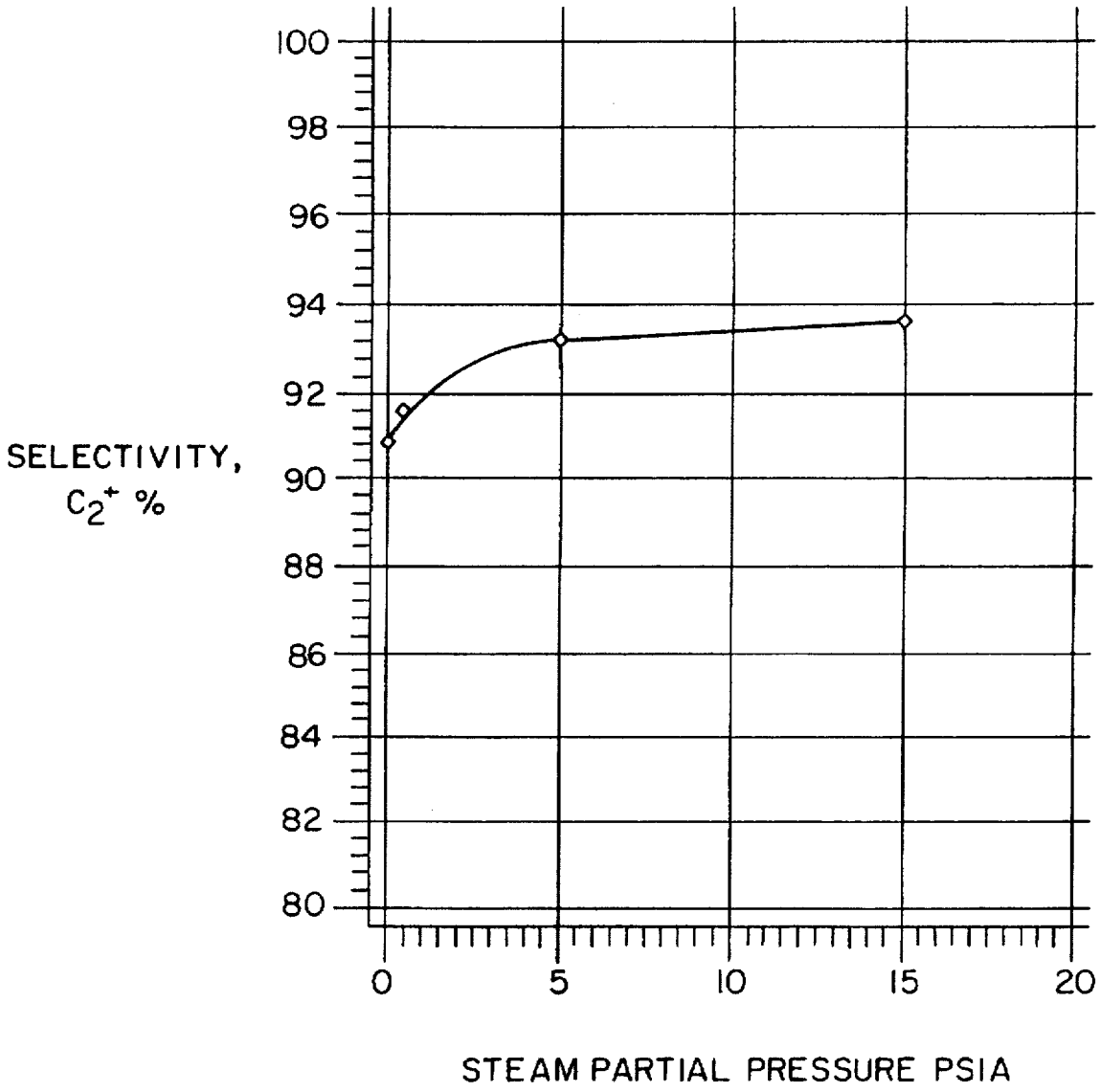
FIGS. 1 and 2 are plots respectively of the effect of steam partial pressure vs $C_2^+$ hydrocarbon selectivity and steam partial pressure vs. $CO_x$ formation rate from the tests described in Example 7.

In addition to methane the methane feedstock, employed in the method of this invention may contain other hydrocarbon or non-hydrocarbon components. The methane content of the hydrocarbon portion of the feedstock however, will typically be within the range of about 40 to 100 vol. %, preferably within the range of about 80 to 100 vol. %, more preferably within the range of about 90 to 100 vol. %.

The gaseous oxidant cofed with methane to the contacting zone preferably comprises a gas containing molecular oxygen (e.g., air). However, oxides of nitrogen, esp. $N_2O$, have also been found to be effective gaseous oxidants. See U.S. Pat. No. 4,547,610, the entire content of which is incorporated herein by reference.

The ratio of hydrocarbon feedstock to oxygen-containing gas is not narrowly critical to the present invention. Generally, it is desirable to control the hydrocarbon/oxygen molar ratio to avoid the formation of gaseous mixtures within the flammable region. Preferably, the ratio is maintained within the range of about 0.1–300:1, more preferably within the range of about 1–150:1. Methane/air feed mixtures containing about 30 to 90 volume % methane have been found to comprise a desirable feedstream. Further dilution of the feedstream with gases such as nitrogen may be beneficial for improved temperature control.

The amount of added water present during at least a portion of the methane/solid contacting may vary over a wide range. Preferably, the mole ratio of added water to methane in the gas to be contacted is less than about 10. More preferably, this mole ratio is in the range of about 0.01 to about 6, still more preferably about 0.05 to about 4.0. The added water may be combined with the methane-containing gas and/or the oxygen-containing gas prior to the contacting the nonacidic solid. For example, the methane-containing gas or the oxygen-containing gas may be contacted with water so that the gas "picks-up" a predetermined, controlled amount of added water prior to the methane/solid contacting. Alternately, a predetermined, controlled amount of water e.g., steam, can be injected into the methane-containing gas and/or the oxygen-containing gas and/or directly into the methane/solid contacting zone or zones.

The solids useful in the present invention are characterized as "nonacidic". This description is meant to refer to the main, predominant surface properties of the nonacidic solids. For example some solid bases are known to have acidic properties to some extent. See Tanabe, K., "Solid Acid and Base Catalysts." In: Catalysis Science & Technology, vol. 2 (New York, Springer-Verlag Berlin Heidelberg, 1981). Currently preferred nonacidic solids used in the present process are characterized by negligible acidity (less than about 0.01 meg/gm) in the $H_o$ range less than about 3.3, preferably less than about 6.8. $H_o$ is the Hammett acidity parameter described on pp. 234–241 of Tanable.

A further characteristic of preferred nonacidic solids for the present process is a relatively low surface area. Nonacidic solids having surface areas less than about 50 $cm^2/gm$ are suitable, but the surface areas of preferred solids are within the range of about 0.1–10 $m^2/gm$.

In one distinct embodiment of this invention methane and a gaseous oxidant are contacted with a nonacidic solid characterized by the substantial absence of reducible metal oxides. Characteristics of nonacidic acids preferred for this embodiment are that they be stable and substantially non-reducible under process conditions. Examples of suitable nonacidic solids include those solid bases described in Table 2 on p. 233 of Tanabe, supra. However, presently preferred nonacidic solids are metal oxides and mixed oxides. Alkaline earth oxides are particularly preferred, especially MgO and CaO. Other suitable metal oxides are $SiO_2$, alpha-$Al_2O_3$, $La_2O_3$, $ThO_2$, $TiO_2$, and $ZrO_2$. Such materials are relatively stable under the conditions of the present process.

Alkali metal-promoted alkaline earth oxides are preferred nonacidic solids for this embodiment. Such solids are described and exemplified in commonly-assigned U.S. patent application Ser. No. 738,110, filed May 24, 1985, the entire content of which is incorporated herein by reference. Halogen promoters may be employed, but in such event, the use of alkali metal promoters is not preferred. See commonly-assigned U.S. patent application Ser. No. 738,114, filed May 24, 1985, the entire content of which is incorporated herein by reference.

In another distinct embodiment of this invention, methane and a gaseous oxidant are contacted with solid comprising a reducible metal oxide. While such solids are sometimes referred to as "catalysts" it will be understood that, under conditions of use, nonacidic solids comprising a reducible metal oxide act as selective oxidants, and, therefore, take on the characteristics of a reactant during use. Thus, for example, the term "Mn-containing oxides" is meant to embrace both reducible oxides of Mn and reduced oxides of Mn, it being understood reducible oxides comprise the principal active component of the compositions.

In their active state, such catalysts comprise at lease one reducible oxide of at least one metal, which oxide when contacted with methane at synthesizing conditions (e.g., at a temperature within the range of about 500° to 1000° C.) produces higher hydrocarbon products, coproduct water, and a reduced metal oxide. The term "reducible" is used to identify those oxides of metals which are reduced under the aforesaid conditions. The term "reducible oxides of metals" includes: (1) compounds described by the general formula $M_2O_y$ wherein M is a metal and x and y designate the relative atomic proportions of metal and oxygen in the composition and/or (2) one or more oxygen-containing metal compounds (i.e., compounds containing elements in addition to the metal and O), provided that such oxides and compounds have the capability of producing higher hydrocarbon products from methane as described herein.

Effective agents for the conversion of methane to higher hydrocarbons have previously been found to comprise reducible oxides of metals selected from the group consisting of manganese, tin, indium, germanium, antimony, lead, bismuth and mixtures thereof. See U.S. Pat. Nos. 4,443,649; 4,444,984; 4,443,648; 4,443,645; 4,443,647; 4,443,644; and 4,443,646. Reducible oxides of manganese are particularly preferred catalyst components.

Reducible oxides of cerium, praseodymium, and terbium have also been found to be effective for the conversion of methane to higher hydrocarbons, particularly associated with an alkali metal component and/or an alkaline earth metal component. See U.S. Pat. Nos. 4,499,324 (Ce) and 4,499,323 (Pr) and also see commonly-assigned U.S. patent application Ser. No. 06/600,918 (Tb).

Reducible oxides of iron and ruthenium are also effective, particularly when associated with an alkali or alkaline earth component. See commonly-assigned U.S. patent application Ser. No. 06/600,730 (Fe) and U.S. Pat. Nos. 4,489,215 and 4,593,139 (Ru).

Alkali and alkaline earth metals and compounds thereof have been found to improve the hydrocarbon product selectivity of reducible metal oxides. The further incorporation of phosphorus into solids promoted by alkali or alkaline earth components enhances catalyst stability. See commonly-assigned U.S. Pat. Nos. 4,499,322 and 4,495,374, the entire content of which are incorporated herein by reference. Alkali metals are selected from the group consisting of lithium, sodium, potassium, rubidium and cesium. Lithium, sodium and potassium, and especially lithium and sodium, are preferred alkali metals. Alkaline earth metals are selected from the group consisting of magnesium, calcium, strontium and barium. Presently preferred members of this group are magnesium and calcium. Compositions derived from magnesia have been found to be particularly effective catalytic materials. Boron and compounds thereof are also desirably present in the reducible metal oxide catalyst employed in the process of this invention. See commonly-assigned U.S. patent application Ser. No. 06/877,574, entire content of which is incorporated herein by reference. One class of boron-promoted compositions useful in the process of this invention comprises:

(1) at least one reducible metal oxide, (2) at least one member of the group consisting of boron and compounds thereof, and (3) at least one member of the group consisting of oxides of alkaline earth metals.

A related class of catalyst compositions further comprises at least one alkali metal or compound thereof. Sodium and lithium are preferred alkali metal components.

One further, special class of catalyst compositions useful in the process of this invention are mixed oxides of sodium, magnesium, manganese and boron characterized by the presence of the crystalline compound $NaB_2Mg_4Mn_2O_x$ wherein x is the number of oxygen atoms required by the valence states of the other elements, said compound having a distinguishing x-ray diffraction pattern. In its most active form, the compound is believed to correspond to the formula $NaB_2Mg_4Mn_2O_{11}$. While this crystalline compound has been found to be associated with highly effective oxidant compositions, it has further been found that still better results are obtained when the oxidant is characterized by both: (1) the presence of crystalline compound $NaB_2Mg_4Mn_2O_x$ and (2) a stoichiometric excess of of Mn relative to at least one of the other elements of the crystalline compound. In currently preferred oxidants of this type, a stoichiometric excess of Mn relative to B is provided. In a still more specific preferred embodiment excess amounts of Na and Mg, as well as Mn, are present in the mixed oxide composition relative to the amounts required by the amount of boron present to satisfy the stoichiometry of the compound $NaB_2Mg_4Mn_2O_x$.

Further examples of components which may be present in the catalysts used in the process of this invention are halogen and chalcogen components. Such components may be added either during preparation of the catalysts or during use. Methane conversion processes employing halogen-promoted reducible metal oxides are disclosed in U.S. Pat. No. 4,544,784. Methane conversion processes employing chalcogen-promoted, reducible metal oxides are disclosed in U.S. Pat. No. 4,544,785.

The reducible metal oxides compositions may be supported by or diluted with support materials such as silica, alumina, titania, zirconia and the like, and combinations thereof. When supports are employed, alkaline earth oxides, especially magnesia, are preferred.

The catalysts are conveniently prepared by any of the methods associated with similar compositions known in the art. Thus, such methods as precipitation, co-precipitation, impregnating, granulation, spray drying or dry-mixing can be used. Supported solids may be prepared hy methods such as adsorption, impregnation, precipitation co-precipitation, and dry-mixing. For example, compounds of Mn,Sn,In,Ge, Pb,Sb,Bi,Pr,Tb,Ce,Fe and or Ru may be combined with compounds of other components in any suitable way. Substantially any compound of the components can be employed. Compounds typically used would be oxides or organic or inorganic salts of the recited components.

To illustrate, when preparing a catalyst containing: (1) a reducible metal oxide component (e.g., Mn), (2) an alkali metal component, (3) a boron component and (4) an alkaline earth component; one suitable method of preparation is to impregnate compounds of the fourth component of the composition with solutions of compounds of Mn, alkali metals, and/or boron. Suitable compounds for impregnation include the acetates, acetyl acetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solid is calcined at a temperature selected within the range of about 300° to 1200° C. Particular calcination temperatures will vary depending on the compounds employed. Preferably, the alkaline earth component is provided as the oxide. Preferably, the alkali metal component is provided as a basic composition of the alkali metal(s). Examples are sodium hydroxide, sodium acetate, lithium hydroxide, lithium acetate, etc. When P is employed as an additive, it has been found desirable to add the alkali metal and P to the composition as compounds such as the orthophosphates, metaphosphates and pyrophosphates of alkali metals. Pyrophosphates are preferred. Sodium pyrophosphate is particularly preferred. Preferably, the boron component is provided as boric acid, boric oxide (of anhydride), alkali metal borates, boranes, borohydrides, etc., especially boric acid or oxide.

Formation of the crystalline compound $NaB_2Mg_4Mn_2O_x$ may be accomplished by reacting active compounds of the substituent elements. A suitable mixture of the reactive compounds is formed and heated for a time sufficient to form the crystalline material. Typically, a temperature of about 850° to about 950° C. is sufficient. When preparing mixed oxide compositions characterized by the presence of the crystalline compound, the composition is desirably incorporated with binders or matrix materials such as silica, alumina, titania, zirconia, magnesia and the like.

Regardless of which particular catalyst is prepared or how the components are combined, the resulting composite will generally be dried and calcined at elevated temperatures prior to use. Calcination can be done under air, $H_2$, carbon oxides, steam, and/or inert gases such as $N_2$ and the noble gases.

Preferably, methane is contacted with reducible metal oxides in the presence of added water and in the substantial absence of catalytically effective nickel, noble metals and compounds thereof, (i.e., nickel, rhodium, palladium, silver, osmium, iridium, platinum and gold) to minimize the deleterious catalytic effects thereof. These metals, when contacted with methane at the temperatures employed in the methane contacting step of the present invention, tend to promote coke formation, and the metal oxides tend to promote the formation of combustion products rather than the desired hydrocarbons. The term "catalytically effective" is used herein to identify the quantity of one or more of nickel and the noble metals and compounds thereof which substantially changes the distribution of products obtained in the method of this invention relative to such contacting in the absence of such metals and compounds thereof.

Regardless of which class of contacting solid is selected (i.e., reducible or nonreducible solid), operating temperatures are generally within the range of about 300° to about 1200° C.

If nonacidic solids are employed without the presence of reducible metal oxides, operating temperature are preferably within the range of about 700° to about 1200° C., more preferably about 800° to about 1000° C.

If reducible metal oxides are employed, the temperature selected may depend in part on the particular reducible metal oxide(s) employed. Best results for contact solids containing manganese have been found at operating temperatures within the range of about 800 degrees to 900 degrees C. Reducible oxides of certain metals may require operating temperatures below the upper part of the recited range to minimize sublimation or volatilization of the metals (or compounds thereof) durin methane contact. Examples are: (1) reducible oxides of indium, (operating temperatures will preferably not exceed about 850° C.,); (2) reducible oxides of germanium (operating temperatures will preferably not exceed about 850° C.); and (3) reducible oxides of bismuth (operating temperatures will preferably not exceed about 800° C.).

Operating pressures are not critical to the presently claimed invention. However, both general syste pressure and partial pressures of methane and water have have been found to effect overall results. Preferred general system pressures are within the range of about 0.1 to 30 atmospheres.

The space velocity of the gaseous reaction streams are similarly not critical to the presently claimed invention, but have been found to effect overall results. Preferred total gas hourly space velocities ar within the range of about 100 to 300,000 $hr.^{-1}$, more preferably within the range of about 600 to 100,000 $hr^{-1}$.

Contacting methane and a reducible metal oxide to form higher hydrocarbons from methane also produces coproduct water and reduces the metal oxide. The exact nature of the reduced metal oxides are unknown, and so are referred to as "reduced metal oxides". Regeneration of reducible metal oxides in the method of the present invention occurs "in situ"-by contact of the reduced metal oxide with the oxygen cofed with methane to the contact zone.

The solids may be maintained in the contact zone as fixed, moving, or fluidized beds of solids. A fixed bed of contact solids is currently preferred for the method of this invention.

The effluent from the contact zone contains higher hydrocarbon products (e.g., ethylene, ethane and other lighter hydrocarbons), carbon oxides, water and unreacted hydrocarbons (e.g., methane). Higher hydrocarbons may be recovered from the effluent and, if desired, subjected to further processing using techniques known to those skilled in the art. Unreacted methane may be recovered and recycled to the contact zone.

The invention is further illustrated by reference to the following examples.

COMPARATIVE EXAMPLE A AND EXAMPLES 1–2

A gaseous feedstream of air/methane and, in Example 1 steam, was contacted with solid MgO (supplied by Kaiser Chemicals) which was impregnated with lithium to contain 0.36% by weight of lithium, calculated as elemental metal. Results are shown in Table I.

TABLE I

| | Comparative Example A | Example 1 | Example 2* |
|---|---|---|---|
| Temperature, °C. | 909 | 884 | 897 |
| Methane GHSV $hr.^{-1}$ | 23,700 | 25,000 | 25,000 |
| Total Pressure, Psia | 19.7 | 34.7 | 19.7 |
| $O_2$ Partial Pressure, Psi | 0.55 | 0.52 | 0.52 |
| $CH_4$ Partial Pressure, Psi | 7.56 | 7.97 | 7.96 |
| $H_2O$ Partial Pressure, Psi | 0 | 15.0 | 0 |
| $CH_4$ Conversion, % | 1.44 | 10.1 | 3.76 |
| $O_2$ Converion, % | 8.36 | 58.0 | 21.3 |
| $C_2$ + Selectivity, % | 86.9 | 93.5 | 91.5 |

*Note:
Steam was excluded from the feed to the contacting zone for 45 minutes before the Example 2 sample was collected.

These Examples were run one after the other in the order shown.

These results demonstrate certain of the substantial benefits of the present invention. For example, the presence of water during the contacting provides for increased methane conversion, oxygen conversion and selectivity to the valuable $C_{2+}$ hydrocarbons. In addition, comparing Example 2 to Example 1 and Comparative Example A suggests that certain of the beneficial effects of added water may last after water addition is complete. Thus, it is possible to obtain at least a portion of the benefits of water addition by periodic, rather than continuous addition of water.

EXAMPLES 3–6 and COMPARATIVE EXAMPLES B–C

A contact solid consisting of 15% by weight manganese (calculated as elemental metal) and 5% by weight $Na_4P_2O_7$ on silica was prepared by impregnating the silica support with appropriate amounts of sodium pyrophosphate and manganese (as manganese acetate). The impregnated solid was dried and then calcined in air.

A quartz tube reactor was charged with the calcined solids. A series of experiments were run at one atmosphere total pressure using a gaseous mixture of 10% by volume of air in methane to contact these calcined solids. When steam was added it equaled 14% of the total number of moles of ethane and air fed to the reactor.

Results are shown in Table II.

TABLE II

| | EXAMPLE | | | | | |
|---|---|---|---|---|---|---|
| | B | C | 3 | 4 | 5 | 6 |
| Temperature. °C. | 900 | 900 | 900 | 899 | 900 | 900 |
| $CH_4$ GHSV, $hr.^{-1}$ | 15000 | 15000 | 15000 | 15000 | 15000 | 15000 |
| Steam Added | No | No | Yes | Yes | Yes | Yes |
| $CH_4$ Conversion, % | 2.8 | 2.7 | 3.5 | 3.1 | 3.1 | 3.7 |
| $O_2$ Conversion, % | 83.5 | 81.6 | — | 68.6 | 66.9 | 74.2 |
| $C_2$ – Selectivity, % | 21.9 | 20.3 | 30.6 | 28.4 | 29.3 | 33.5 |
| $C_2$ Selectivity, % | 40.1 | 40.4 | 44.7 | 43.8 | 46.6 | 40.5 |
| $C_3$ Selectivity, % | 1.6 | 1.4 | 2.6 | 2.7 | 2.2 | 3.7 |

TABLE II-continued

| | EXAMPLE | | | | | |
|---|---|---|---|---|---|---|
| | B | C | 3 | 4 | 5 | 6 |
| $>C_4$ Selectivity, % | 0 | 0 | 0.2 | 0.2 | 0 | 0.3 |
| $C_2$ + Selectivity, % | 63.7 | 62.0 | 78.1 | 75.1 | 78.1 | 77.9 |

These results demonstrate certain of the benefits of the present invention. For example, the presence of steam during the methane/air/contact solids contacting does provide for generally high selectivity to valuable $C_{2+}$ hydrocarbons.

EXAMPLE 7

A series of runs were made using the Li/MgO described in Comparative Example A and Examples 1–2. Partial pressure of methane ranged from about 7.5 to 8.0 psia and that of oxygen from about 0.5 to 0.62 psia. Partial pressure of steam ranged from about 0.5 to 15 psia. Methane GHSV ranged from about 23,700 to 25,000 $hr.^{-1}$ and temperature from about 884° to 909° C.

Figure 2:
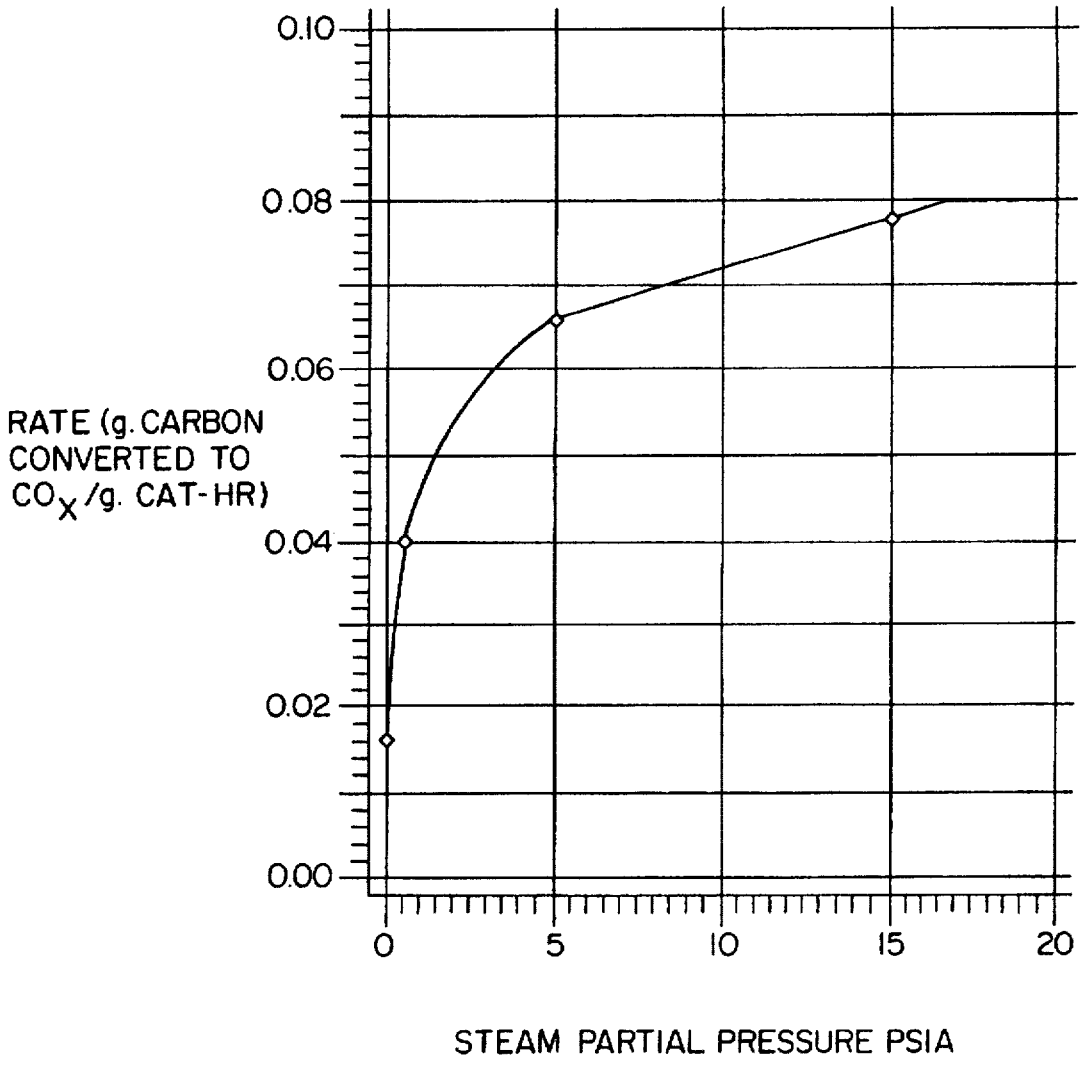

The results achieved are depicted graphically in attached FIGS. 1 and 2. Referring to FIG. 1, it can be seen that the addition of steam to the feed mixture has a substantial effect on the selectivity of the reaction to the desired $C_2^+$ hydrocarbon products.

As shown in FIG. 2, the reaction rate is increased by a very significant extent by the addition of steam to the feed.

While this invention has been described with respect to various specific examples and embodiments, it is to be understood that the invention is not limited thereto and that it can be variously practiced within the scope of the following claims.

What is claimed is:

[1. In a method for converting methane to higher hydrocarbons wherein a gas comprising methane and a gaseous oxidant are contacted with a nonacidic solid to produce higher hydrocarbons and coproduct water, the improvement which comprises conducting at least a portion of said contacting in the presence of added water.]

[2. The method of claim 1 wherein said solid comprises at lease one reducible metal oxide of at least one metal.]

[3. The method of claim 1 wherein the mole ratio of said added water to said methane in said gas is less than about 10.]

[4. The method of claim 1 wherein the mole ratio of said added water to said methane in said gas is in the range of about 0.01 to about 6.]

[5. The method of claim 1 wherein the mole ratio of said added water to said methane in said gas is in the range of about 0.05 to about 4.0.]

[6. The method of claim 1 wherein the contacting is conducted at a temperature within the range of about 300° to about 1200° C.]

[7. The method of claim 1 wherein the contacting is conducted at a temperature of about 700° to about 1200° C.]

[8. The method of claim 1 wherein the contacting is conducted at a temperature of about 800° to about 1000° C.]

[9. The method of claim 3 wherein the contacting is conducted at a temperature of about 500° to about 1000° C.]

[10. The method of claim 1 wherein said solid is selected from the group consisting of basic metal oxides.]

[11. The method of claim 10 wherein said solid is selected from the group consisting of alkaline earth oxides and mixtures thereof.]

[12. The method of claim 10 wherein said solid comprises magnesia.]

[13. The method of claim 10 wherein said solid comprises CaO.]

[14. The method of claim 10 wherein said solid comprises titania.]

[15. The method of claim 10 wherein said solid comprises $SiO_2$.]

[16. The method of claim 10 wherein said solid comprises barium.]

[17. The method of claim 2 wherein said solid is substantially nonreducible under the contacting conditions.]

[18. The method of claim 11 wherein said solid further comprises at least one alkali metal component.]

[19. The method of claim 18 wherein the alkali metal component is selected from the group consisting of sodium and compounds thereof.]

[20. The method of claim 18 wherein the alkali metal component is selected from the group consisting of lithium and compounds thereof.]

[21. The method of claim 18 wherein the alkali metal component is selected from the group consisting of potassium and compounds thereof.]

[22. The method of claim 1 wherein the gaseous oxidant comprises molecular oxygen.]

[23. The method of claim 1 wherein the gaseous oxidant comprises oxides of nitrogen.]

[24. The method of claim 23 wherein the oxides of nitrogen comprises $N_2O$.]

25. In a method for converting methane into higher hydrocarbon products and coproduct water which comprises contacting a gas comprising methane and an oxygen-containing gas with a solid comprising at least one reducible metal oxide of at least one metal, which oxide when contacted with methane at 500° to 1000° C. produces higher hydrocarbons, coproduct water, and reduced metal oxide, the improvement comprising conducting at least a portion of the contacting in the presence of added water.

26. The method of claim 25 wherein the mole ratio of said added water to said methane in said gas is less than about 10.

27. The method of claim 25 wherein the mole ratio of said added water to said methane in said gas is in the range of about 0.01 to about 6.

28. The method of claim 25 wherein the mole ratio of said added water to said methane in said gas is in the range of about 0.05 to about 4.0.

29. The method of claim 25 wherein the solid comprises at least one reducible oxide of Mn.

30. The method of claim 29 wherein the solid comprises at least one member of the group consisting of alkali metals, alkaline earth metals, and compounds and mixtures thereof.

31. The method of claim 29 wherein the solid comprises at least one member of the group consisting of boron and compounds thereof.

32. The method of claim 30 wherein the solid comprises at least one member of the group consisting of boron and compounds thereof.

* * * * *